(12) United States Patent
Vartuli et al.

(10) Patent No.: US 7,985,883 B2
(45) Date of Patent: Jul. 26, 2011

(54) PROCESS FOR OXIDIZING ALKYLAROMATIC COMPOUNDS

(75) Inventors: James C. Vartuli, West Chester, PA (US); Jihad M. Dakka, Whitehouse Station, NJ (US); Robert C. Lemon, Easton, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 12/601,578

(22) PCT Filed: Jul. 8, 2008

(86) PCT No.: PCT/EP2008/005627
§ 371 (c)(1),
(2), (4) Date: Apr. 13, 2010

(87) PCT Pub. No.: WO2009/010224
PCT Pub. Date: Jan. 22, 2009

(65) Prior Publication Data
US 2010/0217048 A1 Aug. 26, 2010

Related U.S. Application Data (60) Provisional application No. 60/950,008, filed on Jul. 16, 2007.

(51) Int. Cl.
C07C 45/53 (2006.01)
C07C 37/08 (2006.01)
C07C 407/00 (2006.01)
(52) U.S. Cl. .......... 568/376; 568/568; 568/798
(58) Field of Classification Search .......... 568/376, 568/568, 798
See application file for complete search history.

(56) References Cited

U.S. PATENT DOCUMENTS

| | | | |
|---|---|---|---|
| 3,214,236 | A | 10/1965 | Weisz et al. |
| 5,183,945 | A | 2/1993 | Stibrany et al. |
| 5,340,562 | A | 8/1994 | O'Young et al. |
| 5,523,509 | A | 6/1996 | O'Young et al. |
| 5,922,920 | A | 7/1999 | Bond et al. |
| 6,720,462 | B2 | 4/2004 | Kuhnle et al. |
| 6,852,893 | B2 | 2/2005 | Kuhnle et al. |

FOREIGN PATENT DOCUMENTS

| | | |
|---|---|---|
| EP | 0 710 622 | 5/1996 |
| WO | 2006/015826 | 2/2006 |

OTHER PUBLICATIONS

Brock, S. et al. "A Review of Porous Manganese Oxide Materials", Chemical Material, 1998, vol. 10, pp. 2619-2628.
Ghosh, R. et al. "Liquid-Phase Epoxidation of Olefins by Manganese Oxide Octahedral Molecular Sieves" Journal of Catalysis, 2004, vol. 224, pp. 288-296.
Ghosh, R. et al. "Liquid-Phase Epoxidation of Olefins by Manganese Oxide Octahedral Molecular Sieves" Journal of Catalysis, 2004, vol. 224, pp. 288-296.
Miyake, T. et al., "Synthesis of Al-Containing Octahedral Molecular Sieves and Oxidation of Cyclohexane with Them" Applied Catalysis A: General, 2005, vol. 288, No. 1-2, pp. 216-219.
Shen Y.F. et al., "Manganese Oxide Octahedral Molecular Sieves: Preparation, Characterization, and Applications", Science, 1993, vol. 260, pp. 511-515.
Suib, S. "Microporous Manganese Oxides" Current Opinion in Solid State and Materials Science, 1998, vol. 3, pp. 63-70.
Turner, S. et al., "Todorokites: A New Family of Naturally Occurring Manganese Oxides", Science, 1981, vol. 212, pp. 1024-1026.
Vertivel, S. et al., "Co and Mn Impregnated MCM-41: Their Applications to Vapour Phase Oxidation of Isopropylbenzene" Journal of Molecular Catalysis A: Chemical, 2005, vol. 227, No. 1, pp. 269-278.
Wang, J-Y et al., "Cyclohexane Functionalization Catalyzed by Octahedral Molecular Sieve (OMS-1) Materials" Journal of Catalysis, 1998, vol. 176, No. 2, pp. 275-284.
O'Young, C-L, "Hydrothermal Synthesis of Manganese Oxides with Tunnel Structures," Synthesis of Microporous Materials, Van Nostrand Reinhold, NY, 1992, vol. 2, pp. 333-340.

(Continued)

*Primary Examiner* — Sikarl Witherspoon
(74) *Attorney, Agent, or Firm* — Jamie Sullivan (57) ABSTRACT

In a process for producing hydroperoxides, an alkylaromatic compound of general formula (I):

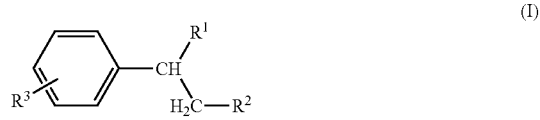

in which $R^1$ and $R^2$ each independently represents an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, with oxygen in the presence of a catalyst comprising a manganese oxide molecular sieve to produce a hydroperoxide of general formula (II):

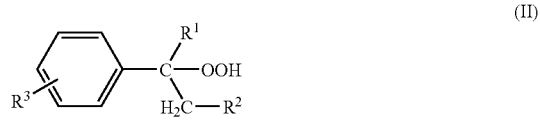

in which $R^1$, $R^2$ and $R^3$ have the same meaning as in formula (I).
The hydroperoxide of formula (II) may then be converted to a phenol and an aldehyde or a ketone of the general formula $R^1COCH_2R^2$ (III), in which $R^1$ and $R^2$ have the same meaning as in formula (I). In the case where the ketone is cyclohexanone, this may then be dehydrogenated to produce further phenol.

23 Claims, 3 Drawing Sheets

OTHER PUBLICATIONS

Chang, C.D. et al., "Manganese Nodules as Demetalation Catalysts" Ind. Eng. Chem., Process Des. Develop., 1974, vol. 13, No. 3, pp. 315-316.

"Phenol", Process Economics Report No. 22B, Stanford Research Institute, Dec. 1977, pp. 113-121 and 261, 263.

Sheldon R. A. et al, "Organocatalytic Oxidations Mediated by Nitroxyl Radicals" *Adv. Synth. Catal.*, 2004, vol. 346, pp. 1051-1071.

Wu, S-C., et al., "*Use of Deep Sea Manganese Nodules as Catalysis for Reduction of Nitric Oxide with Ammonia*" Atmospheric Environment, 1972, vol. 6, pp. 309-317.

PROCESS FOR OXIDIZING ALKYLAROMATIC COMPOUNDS

CROSS-REFERENCE TO RELATED APPLICATIONS

This application is a National Stage Application of International Application No. PCT/EP2008/005627 filed Jul. 8, 2008, which claims priority from U.S. Ser. No. 60/950,008 filed Jul. 16, 2007, both of which are incorporated herein by reference.

FIELD

The present invention relates to a process for oxidizing alkylaromatic compounds, and in one embodiment includes a process for producing phenol and substituted phenols.

BACKGROUND

Phenol and substituted phenols are important products in the chemical industry and are useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene relative to that of butenes is likely to increase, due to a developing shortage of propylene.

Thus, a process that uses butenes or higher alkenes instead of propylene as feed and coproduces methyl ethyl ketone (MEK) or higher ketones, such as cyclohexanone, rather than acetone may be an attractive alternative route to the production of phenols. For example, there is a growing market for MEK, which is useful as a lacquer, a solvent and for dewaxing of lubricating oils. In addition, cyclohexanone is used as an industrial solvent, as an activator in oxidation reactions and in the production of adipic acid, cyclohexanone resins, cyclohexanone oxime, caprolactam and nylon 6.

It is known that phenol and MEK can be produced from sec-butylbenzene, in a process where sec-butylbenzene is oxidized to obtain sec-butylbenzene hydroperoxide and the peroxide decomposed to the desired phenol and methyl ethyl ketone. An overview of such a process is described in pages 113-121 and 261-263 of Process Economics Report No. 22B entitled "Phenol", published by the Stanford Research Institute in December 1977.

However, in comparison to cumene, oxidation of aromatic compounds substituted by branched alkyl groups having 4 or more carbon atoms, such as sec-butylbenzene, to the corresponding hydroperoxide requires higher temperatures and is very sensitive to the presence of impurities. For example, in the case of sec-butylbenzene containing 1% by weight of isobutylbenzene, the rate of formation of sec-butylbenzene hydroperoxide decreases to about 91% of that when the sec-butylbenzene is free of isobutylbenzene. Similarly, when the isobutylbenzene content is 1.65% by weight, the rate of oxidation decreases to about 86%; when the isobutylbenzene content is 2% by weight, the rate of oxidation decreases to about 84%; and when the isobutylbenzene content is 3.5% by weight, the rate of oxidation decreases to as low as about 82%.

Thus there remains a need to find an oxidation process for producing for example $C_4+$ alkyl aromatic hydroperoxides, and particularly sec-butylbenzene hydroperoxide, that is much less sensitive to the presence of impurities than the existing oxidation processes, and that allows efficient commercial scale production of phenol and MEK or higher ketones.

U.S. Pat. Nos. 6,852,893 (Creavis) and 6,720,462 (Creavis) describe methods for producing phenol by catalytic oxidation of alkylaromatic hydrocarbons to the corresponding hydroperoxide, and subsequent cleavage of the hydroperoxide to give phenol and a ketone. Catalytic oxidation takes place with oxygen, in the presence of a free radical initiator and a catalyst, typically an N-hydroxycarbodiimide catalyst, such as N-hydroxyphthalimide. Preferred substrates that may be oxidized by this process include cumene, cyclohexylbenzene, cyclododecylbenzene and sec-butylbenzene.

In addition, the article by Sheldon et al entitled "Organocatalytic Oxidations Mediated by Nitroxyl Radicals" in *Adv. Synth. Catal.*, 2004, 346, pages 1051-1071 discloses that cyclohexylbenzene (CHB) can be oxidized to the 1-hydroperoxide with 97.6% selectivity at 32% CHB conversion at 100° C. in the presence of 0.5 mol % of a N-hydroxyphthalimide catalyst and 2 mol % of the product hydroperoxide as a free radical initiator.

However, while N-hydroxycarbodiimides have shown activity and selectivity for the oxidation of alkylaromatic compounds to their corresponding hydroperoxides, they suffer from the problems inherent in any homogeneous catalyst in that they are tend to be removed from the reaction zone with the product effluent and so must be separated from the product effluent. There is therefore significant interest in developing a heterogeneous oxidation catalyst for producing alkylaromatic hydroperoxides provided adequate activity and selectivity can still be maintained.

In our International Patent Publication No. WO 06/15826 we have described a process for producing phenol and methyl ethyl ketone, in which a feed comprising benzene and a $C_4$ alkylating agent is contacted under alkylation conditions with catalyst comprising zeolite beta or a molecular sieve having an X-ray diffraction pattern including d-spacing maxima at 12.4±0.25, 6.9±0.15, 3.57±0.07 and 3.42±0.07 Angstrom to produce an alkylation effluent comprising sec-butylbenzene. The sec-butylbenzene is then oxidized to produce a hydroperoxide and the hydroperoxide is cleaved to produce the desired phenol and methyl ethyl ketone. Although homogeneous catalysts, such as N-hydroxy substituted cyclic imides, are disclosed as suitable for the oxidation reaction, preferred catalysts are said to be heterogeneous catalysts, such as the oxo (hydroxo) bridged tetranuclear manganese complexes described in U.S. Pat. No. 5,183,945 and U.S. Pat. No. 5,922,920.

Manganese oxide octahedral molecular sieves possessing mono-directional tunnel structures are also known and constitute a family of molecular sieves wherein chains of $MnO_6$ octahedra share edges to form tunnel structures of varying size. Such materials have been detected in samples of terrestrial origin and are also found in manganese nodules recovered from the ocean floor. Manganese nodules have been described as useful catalysts in the oxidation of carbon monoxide, methane and butane (U.S. Pat. No. 3,214,236 [Mobil]), in the reduction of nitric oxide with ammonia (Atmospheric Environment, Vol. 6, p. 309 (1972)) and in the demetallation of topped crude in the presence of hydrogen (Ind. Eng. Chem. Proc. Dev., Vol. 13, p. 315 (1974)).

The hollandites are naturally occurring hydrous manganese oxides with tunnel structures consisting of double chains of $MnO_6$ octahedra which share edges to form (2×2) tunnel structures. The average size of these tunnels is about 4.6 A° square. Ba, K, Na and Pb ions are present in the tunnels and coordinated to the oxygens of the double chains. The identity of the tunnel cations determines the mineral species. Specific hollandite species include hollandite ($BaMn_8O_{16}$), cryptomelane ($KMn_8O_{16}$), manjiroite ($NaMn_8O_{16}$) and coronadite ($PbMn_8O_{16}$). A hydrothermal method of synthesizing manganese oxide octahedral molecular sieves possessing (2×2) tunnel structures such as those possessed by the naturally-occurring hollandites is described in "Hydrothermal Synthesis of Manganese Oxides with Tunnel Structures," in Synthesis of Microporous Materials, Vol. II, 333, M. L. Occelli, H. E. Robson Eds. Van Nostrand Reinhold, N.Y., 1992. Such synthetic octahedral molecular sieves having (2×2) tunnel structures are referred to in the art by the designation OMS-2.

The todorokites are naturally occurring manganese oxides with (3×3) tunnel structures formed by triple chains of $MnO_6$ edge-sharing octahedra. Todorokites and related species are described by Turner et al. in "Todorokites: A New Family of Naturally Occurring Manganese Oxides", Science, Vol. 212, pp. 1024-1026 (1981). The authors speculate that since todorokites are often found in deep-sea manganese nodules containing high concentrations of copper and nickel, it is probable that such metals substitute for $Mn^{2+}$ in the octahedral framework. Todorokites have attracted particular interest because of their relatively large tunnel dimensions and their cation-exchange behaviour which is similar to that of zeolites (Shen et al., "Manganese Oxide Octahedral Molecular Sieves: Preparation, Characterization, and Applications", Science, Vol. 260, pp. 511-515 (1993)). A method of synthesizing a manganese oxide octahedral molecular sieve possessing (3×3) tunnel structures such as those possessed by the naturally-occurring todorokites is described in U.S. Pat. No. 5,340,562 (Texaco). Such synthetic octahedral molecular sieves having (3×3) tunnel structures are referred to in the art by the designation OMS-1.

Synthetic manganese oxide octahedral molecular sieves of the OMS-1 and OMS-2 type have been employed as acid-base catalysts in a variety of acid-base organic conversion reactions, such as the conversion of alcohols to ketones and olefins. Manganese oxide molecular sieves having a 4×4 tunnel structure, designated OMS-3, have also been synthesized and have been proposed as CO oxidation catalysts, for example in EP-A-0710622 (Texaco).

According to the invention, it has now been found that manganese oxide molecular sieves show activity and selectivity as catalysts in the oxidation of secondary alkyl substituted benzenes, including sec-butylbenzene and cyclohexylbenzene, to the corresponding hydroperoxides.

SUMMARY

In one aspect, the present invention resides in a process for oxidizing an alkylaromatic compound to the corresponding hydroperoxide, the process comprising contacting an alkylaromatic compound of general formula (I):

(I)

in which $R^1$ and $R^2$ each independently represents hydrogen or an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, with oxygen in the presence of a catalyst comprising a manganese oxide molecular sieve.

In one embodiment the process of the invention further comprises converting the hydroperoxide into a phenol and an aldehyde or ketone of the general formula $R^1COCH_2R^2$ (III) in which $R^1$ and $R^2$ have the same meaning as in formula (I). Accordingly, in a further preferred aspect, the present invention resides in a process for producing a phenol, said process comprising:

(a) contacting an alkylaromatic compound of general formula (I):

(I)

in which $R^1$ and $R^2$ each independently represents hydrogen or an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, with oxygen in the presence of a catalyst comprising a manganese oxide molecular sieve to produce a hydroperoxide of general formula (II):

(II)

in which $R^1$, $R^2$ and $R^3$ have the same meaning as in formula (I), and (b) converting the hydroperoxide of formula (II) into a phenol and an aldehyde or ketone of the general formula $R^1COCH_2R^2$ (III), in which $R^1$ and $R^2$ have the same meaning as in formula (I).

Conveniently, said manganese oxide molecular sieve comprises $MnO_6$ octahedra which share edges to form a tunnel structure. Generally, said manganese oxide molecular sieve may be ion-exchanged with one or more metal cations, for example metal cations selected from potassium, sodium, cesium, barium, magnesium, silver and copper. Alternatively, various divalent cations can be included in the synthesis as cationic templates, such as magnesium, cobalt, nickel, copper and zinc. They can be found within the lattice of the resultant molecular sieve as substitutions for the manganese (see reference Shen et. al. JACS 1994, 116, 11020-11029).

Conveniently, said alkylaromatic compound of general formula (I) is selected from ethylbenzene, cumene, sec-butylbenzene, sec-pentylbenzene, p-methyl-sec-butylbenzene, 1,4-diphenylcyclohexane, sec-hexylbenzene, cyclopentylbenzene, cyclohexylbenzene and cyclooctylbenzene, and preferably is sec-butylbenzene or cyclohexylbenzene.

Conveniently, said contacting is conducted at a temperature of about 20° C. to about 300° C., such as about 50° C. to about 130° C. The contacting is conveniently conducted at a pressure of about 15 kPa to about 1000 kPa, such as about 40 kPa to about 250 kPa.

Conveniently, the optional converting of the hydroperoxide to phenol and an aldehyde or ketone [hydroperoxide converting step (b) in the preferred aspect detailed above] is conducted in the presence of a catalyst, such as a homogeneous catalyst, for example at least one of sulfuric acid, perchloric acid, phosphoric acid, hydrochloric acid, p-toluenesulfonic acid, ferric chloride, boron trifluoride, sulfur dioxide and sulfur trioxide.

Alternatively, the hydroperoxide converting may be is conducted in the presence of a heterogeneous catalyst, such as a smectite clay.

Conveniently, the hydroperoxide converting [step (b) in the above preferred aspect] is conducted at a temperature of about 40° C. to about 120° C. and/or a pressure of about 100 to about 1000 kPa and/or a liquid hourly space velocity (LHSV) based on the hydroperoxide of about 1 to about 50 $hr^{-1}$.

DETAILED DESCRIPTION OF THE EMBODIMENTS

The present invention provides a process for oxidizing an alkylaromatic compound of general formula (I):

(I)

in which $R^1$ and $R^2$ each independently represents hydrogen or an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group. The phrase "provided that $R^1$ and $R^2$ may be joined" and so on is used herein to mean that, as an alternative to each of $R^1$ and $R^2$ being a ("monovalent") alkyl group, the two "alkyl" entities designated "$R^1$" and "$R^2$" are joined into a ("divalent") hydrocarbyl chain (having 2 to 8 carbons in that chain), with respective ends of that "divalent" chain being linked to the C atoms specifically shown in formula (I) to form a ring. Thus, in an embodiment, $R^1$ and $R^2$ together constitute a hydrocarbyl moiety that connects to the carbon atoms of formula (I) to form a cyclic group having from 4 to 10 carbon atoms, conveniently a cyclohexyl group, which may be substituted with one or more alkyl group having from 1 to 4 carbon atoms or with one or more phenyl groups. Examples of suitable alkylaromatic compounds are ethylbenzene, cumene, sec-butylbenzene, sec-pentylbenzene, p-methyl-sec-butylbenzene, 1,4-diphenylcyclohexane, sec-hexylbenzene, and cyclohexylbenzene, with sec-butylbenzene and cyclohexylbenzene being preferred. It will also be understood that in the case where $R^1$ and $R^2$ are joined to form a cyclic group, the number of carbons forming the cyclic ring is from 4 to 10. However, that ring may itself carry one or more substituents, such as one or more alkyl groups having from 1 to 4 carbon atoms or one or more phenyl groups, as in the case of 1,4-diphenylcyclohexane.

In one practical embodiment, the alkylaromatic compound of general formula (I) is sec-butylbenzene and is produced by alkylating benzene with at least one $C_4$ alkylating agent under alkylation conditions and in the presence of a heterogeneous catalyst, such as zeolite beta or more preferably at least one molecular sieve of the MCM-22 family (as defined below). The alkylation conditions conveniently include a temperature of from about 60° C. to about 260° C., for example between about 100° C. and about 200° C. and/or a pressure of 7000 kPa or less, for example from about 1000 to about 3500 kPa and/or a weight hourly space velocity (WHSV) based on $C_4$ alkylating agent of between about 0.1 and about 50 $hr^{-1}$, for example between about 1 and about 10 $hr^{-1}$.

The $C_4$ alkylating agent conveniently comprises at least one linear butene, namely butene-1, butene-2 or a mixture thereof. The alkylating agent can also be an olefinic $C_4$ hydrocarbon mixture containing linear butenes, such as can be obtained by steam cracking of ethane, propane, butane, LPG and light naphthas, catalytic cracking of naphthas and other refinery feedstocks and by conversion of oxygenates, such as methanol, to lower olefins. For example, the following $C_4$ hydrocarbon mixtures are generally available in any refinery employing steam cracking to produce olefins and are suitable for use as the $C_4$ alkylating agent: a crude steam cracked butene stream, Raffinate-1 (the product remaining after solvent extraction or hydrogenation to remove butadiene from the crude steam cracked butene stream) and Raffinate-2 (the product remaining after removal of butadiene and isobutene from the crude steam cracked butene stream).

In a further practical embodiment, the alkylaromatic compound of general formula (I) is cyclohexylbenzene and is preferably produced by contacting benzene with hydrogen in the presence of a heterogeneous bifunctional catalyst which comprises at least one metal having hydrogenation activity, typically selected from the group consisting of palladium, ruthenium, nickel and cobalt, and a crystalline inorganic oxide material having alkylation activity, typically at least one molecular sieve of the MCM-22 family (as defined below). The contacting step is conveniently conducted at a temperature of about 50° C. to about 350° C. and/or a pressure of about 100 to about 7000 kPa and/or a benzene to hydrogen molar ratio of about 0.01 to about 100 and/or a WHSV of about 0.01 to about 100.

The term "MCM-22 family material" (or "material of the MCM-22 family" or "molecular sieve of the MCM-22 family" or "MCM-22 family zeolite"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Molecular sieves of the MCM-22 family are preferred as the alkylation catalyst since they have been found to be highly selective to the production of sec-butylbenzene, as compared with the other butylbenzene isomers. Preferably, the molecular sieve is selected from (a) MCM-49, (b) MCM-56 and (c) isotypes of MCM-49 and MCM-56, such as ITQ-2.

The oxidation step in the present process is effected by contacting the alkylaromatic compound with oxygen for example in the form of a gas containing molecular oxygen, such as air, in the presence of an added heterogeneous catalyst comprising a porous manganese oxide molecular sieve. Conveniently, the manganese oxide molecular sieve comprises $MnO_6$ octahedra which share edges to form a 3-dimensional framework tunnel structure having exchangeable metal cations present in the tunnels (tunnel cations). In one embodiment, the tunnel structure is composed of $MnO_6$ octahedra which share edges to form double chains, and the octahedra of the double chains share corners with adjacent double chains to form a 2×2 tunnel structure, such as is present in the naturally occurring manganese mineral hollandite. Such a 2×2 tunnel structure molecular sieve would have generally square cross-section pores with the sides of the square being about 4.6 Å in length. An alternative tunnel structure with larger pores is the 3×3 octahedral molecular sieve corresponding to natural occurring manganese mineral todorokite.

The porous manganese oxide molecular sieve employed herein typically complies with the general formula (IV):

$$[A_{16-a}MaMn_{16-a}O_{32}]_n \qquad \text{(IV)}$$

in which

A represents a tunnel cation that may be in oxidation state +1, +2, +3, +4 or +5, wherein the metal of the cation is selected from the transition metals (Groups 3-12) and metals of Group 1 and Group 2 of the IUPAC Periodic Table of the Elements (1 Nov. 2004);

M represents a lattice cation that may be in oxidation state +1, +2, +3, +4 or +5, wherein the metal of the cation is a transition metal (Groups 3-12) other than manganese;

Mn represents manganese;

a is a number equal to or greater than zero and less than 16, preferably in the range of 0.1 to <16; and n is a number equal to or greater than 1.

The porous manganese oxide may be hydrated, that is, it may have one or more $H_2O$ molecules associated with the general formula (IV). Typically, however, the manganese oxide is dehydrated, such as, by heating at a temperature of at least 200° C., before being used in the present oxidation process.

In the general formula (IV), where there is more than one tunnel cation A then each A may be the same or different with regard to oxidation state and/or metal. Similarly, where the composition contains more than one lattice cation M, then each M may be the same or different with regard to oxidation state and/or metal. Suitable metals for the tunnel cations A include potassium, sodium, cesium, barium, magnesium, silver and copper. Suitable metals for the lattice cations M include magnesium, cobalt, nickel copper and zinc. It will be appreciated that the tunnel cations A, but not the lattice cations M, can generally be replaced by conventional ion exchange techniques.

The manganese oxide molecular sieves employed in the present oxidation process can be produced by any of the synthesis methods known in the art. For example, OMS-2 (2×2 tunnel structure) MnO molecular sieves can be produced by the methods described in "Hydrothermal Synthesis of Manganese Oxides with Tunnel Structures," in Synthesis of Microporous Materials, Vol. II, 333, M. L. Occelli, H. E. Robson Eds. Van Nostrand Reinhold, N.Y., 1992, whereas OMS-1 (3×3 tunnel structure) materials can be produced by the methods described in U.S. Pat. No. 5,340,562 and U.S. Pat. No. 5,523,509 and OMS-3 (4×4 tunnel structure) materials by the methods described in EP-A-0710622, the entire contents of all of which are incorporated herein by reference.

An alternative synthesis method for the production of OMS-2 (2×2 tunnel structure) MnO molecular sieves is provided in our co-pending U.S. Patent Application Ser. No. 60/949,997, filed concurrently herewith.

Suitable conditions for the present oxidation step include a temperature between about 20° C. and about 300° C., such as about 50° C. to about 130° C., and/or a pressure of about 15 to about 1000 kPa, such as about 40 to about 250 kPa. The oxidation reaction is conveniently conducted in a catalytic distillation unit and the hydroperoxide produced may be concentrated by distilling off the unreacted alkylaromatic compound.

The product of the oxidation reaction includes a hydroperoxide of general formula (II):

in which $R^1$, $R^2$ and $R^3$ have the same meaning as in formula (I). Preferably, the hydroperoxide is sec-butylbenzene hydroperoxide or cyclohexylbenzene hydroperoxide. This hydroperoxide can then converted by acid cleavage to phenol (which may be a substituted phenol) and an aldehyde or ketone of the general formula $R^1COCH_2R^2$ (III), in which $R^1$ and $R^2$ have the same meaning as in formula (I).

The cleavage reaction is conveniently effected by contacting the hydroperoxide with a catalyst in the liquid phase at a temperature of about 20° C. to about 150° C., such as about 40° C. to about 120° C., and/or a pressure of about 50 to about 2500 kPa, such as about 100 to about 1000 kPa and/or a liquid hourly space velocity (LHSV) based on the hydroperoxide of about 0.1 to about 100 $hr^{-1}$, preferably about 1 to about 50 $hr^{-1}$. The hydroperoxide is preferably diluted in an organic solvent inert to the cleavage reaction, such as methyl ethyl ketone, phenol or sec-butylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid A suitable heterogeneous catalyst for use in the cleavage of sec-butylbenzene hydroperoxide includes a smectite clay, such as an acidic montmorillonite silica-alumina clay, as described in U.S. Pat. No. 4,870,217 (Texaco), the entire disclosure of which is incorporated herein by reference.

In the case where the alkylaromatic compound that is oxidized according to the invention is cyclohexylbenzene, the oxidation product is cyclohexylbenzene hydroperoxide and the cleavage product comprises phenol and cyclohexanone. The crude cyclohexanone and crude phenol from the cleavage step may be subjected to further purification to produce purified cyclohexanone and phenol. A suitable purification process includes, but is not limited to, a series of distillation towers to separate the cyclohexanone and phenol from other species. The crude or purified cyclohexanone may itself be subjected to dehydrogenation in order to convert it to phenol. Such dehydrogenation may be performed, for example, over a catalyst such as platinum, nickel or palladium.

The invention will now be more particularly described with reference to the following non-limiting Examples.

Example 1

A catalyst was prepared by combining 300 grams of deionized (DI) water, 13.3 grams of potassium permanganate, and 1.6 grams of fumaric acid with stirring at room temperature. The mixture was then allowed to age at room temperature with no stirring then was filtered and washed. A portion of the dried sample was then calcined in air at 300° C. for three hours.

Example 2

A portion of the catalyst of Example 1 before calcination was subjected to ion exchange using the following procedure:
a. a solution was formed by adding 26 grams of solid barium nitrate to 100 grams of DI water;
b. 3 grams of the uncalcined material produced in Example 1 was then added and the solution was stirred for 90 minutes;
c. the pH was adjusted to 5.6 with the addition of 0.4 grams of concentrated nitric acid; and
d. after stirring for an additional hour the exchanged sample was then filtered and washed with DI water and air-dried.

The dried sample was then calcined in air at 300° C. for three hours. Elemental analysis showed that the sample, prior to calcination, contained 46 wt % manganese, 36 wt % barium and the remainder oxygen.

Example 3

A catalyst was prepared by combining 300 grams of DI water, 40 grams of potassium permanganate, and 5 grams of fumaric acid with stirring at room temperature. The mixture was then allowed to age at room temperature with no stirring then was filtered and washed. A portion of the dried sample was then calcined in air at 300° C. for three hours.

Example 4

A portion of the catalyst of Example 3 before calcination was subjected to ion exchange using the following procedure:
a. a solution was formed by adding 26 grams of solid barium nitrate to 200 grams of DI water;
b. 3 grams of the uncalcined material produced in Example 3 was then added and the solution was stirred for 90 minutes;
c. the pH was 7 with no adjustment; and
d. after stirring for an additional hour the exchanged sample was then filtered and washed with DI water and air-dried.

The dried sample was then calcined in air at 300° C. for three hours. Elemental analysis showed the calcined sample to contain (in weight %): Mn—22.8, K—0.25, and Ba—62.4.

Example 5

A further portion of the catalyst of Example 3 before calcination was subjected to ion exchange using the following procedure:
a. a solution was formed by adding 26 grams of solid copper nitrate to 200 grams of DI water;
b. 3 grams of the uncalcined material produced in Example 3 was then added and the solution was stirred for 90 minutes;
c. the pH was adjusted to 7 with the addition of 22.5 grams of concentrated ammonium hydroxide; and
d. after stirring for an additional hour the exchanged sample was then filtered and washed with DI water and air-dried.

The dried sample was then calcined in air at 300° C. for three hours. Elemental analysis showed the calcined sample to contain (in weight %): Mn—15.8, K—0.17, and Cu—63.3.

Example 6

A catalyst was prepared by combining 600 grams of DI water, 80 grams of potassium permanganate, and 10 grams of fumaric acid with stirring at room temperature. The mixture was then allowed to age at room temperature with no stirring then was filtered and washed. A first portion of the dried sample was then calcined in air at 200° C. for two hours, while a second was calcined in air at 300° C. for two hours and a third portion was calcined in air at 400° C. for two hours.

Example 7

A portion of the catalyst of Example 6 before calcination was subjected to ion exchange using the following procedure:
a. a solution was formed by adding 26 grams of solid magnesium nitrate to 200 grams of DI water;
b. 3 grams of the uncalcined material produced in Example 6 was then added and the solution was stirred for 90 minutes;
c. the pH was adjusted to 7 with the addition of 22.5 grams of concentrated ammonium hydroxide; and
d. after stirring for an additional hour the exchanged sample was then filtered and washed with DI water and air-dried.

The dried sample was then calcined in air at 300° C. for three hours. Elemental analysis showed the calcined sample to contain (in weight %): Mn—66.6, K—1.71, and Mg—6.94.

Example 8

Comparative

SBB Oxidation Using NHPI

Figure 1:
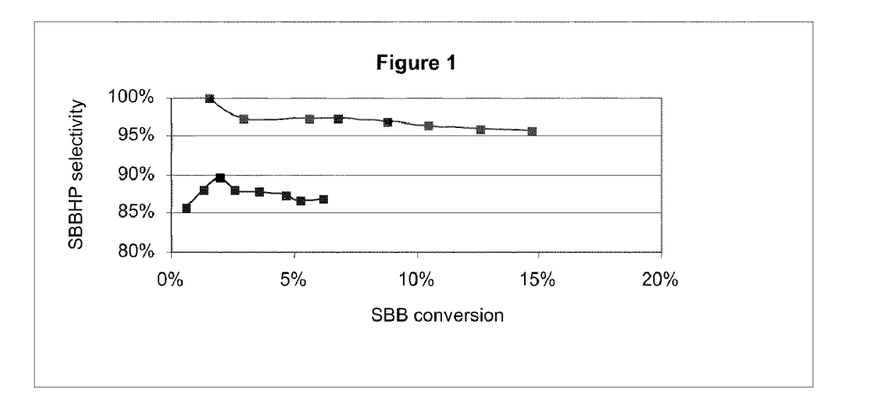
FIG. 1 is a graph comparing sec-butylbenzene (SBB) conversion (%) against sec-butylbenzene hydroperoxide (SBBHP) selectivity (%) for the N-hydroxyphthalimide (NHPI) catalyst used in Example 8 [upper line] and for the MnO molecular sieve catalyst of Example 1 [lower line].

To a 250-ml round bottom flask fitted with a condenser, stirrer and an air sparger, was charged 100 g of sec-butylbenzene (SBB), as supplied by TCI, and 0.2375 g of N-hydroxyphthalimide (NHPI). The flask was heated using a temperature-controlled heating mantle. Reaction temperature was 115° C. Reaction pressure was approximately atmospheric. The air flow rate was approximately 220 cc/min. Every 45 minutes, a small aliquot of the reaction mixture was removed from the flask and analyzed by GC. The test was run for 6 hours. A graph of the SBB conversion against the selectivity to sec-butylbenzene hydroperoxide (SBBHP) is shown in FIG. 1 [upper plot].

Example 9

SBB Oxidation Using Example 1 Catalyst

To a 250-ml round bottom flask fitted with a condenser, stirrer and an air sparger, was charged 100 g of sec-butylbenzene (TCI) and 0.2 g of the catalyst of Example 1. The flask was heated using a temperature-controlled heating mantle. Reaction temperature was 115° C. Reaction pressure was approximately atmospheric. The air flow rate was approximately 220 cc/min. Every 45 minutes, a small aliquot of the reaction mixture was removed from the flask and analyzed by GC. The test was run for 6 hours. A graph of the SBB conversion against the selectivity to sec-butylbenzene hydroperoxide (SBBHP) is shown in FIG. 1 [lower plot]. The catalyst performance shows a flat selectivity of around 87% at any conversion.

Example 10

SBB Oxidation Using Example 2 Catalyst

Figure 2:
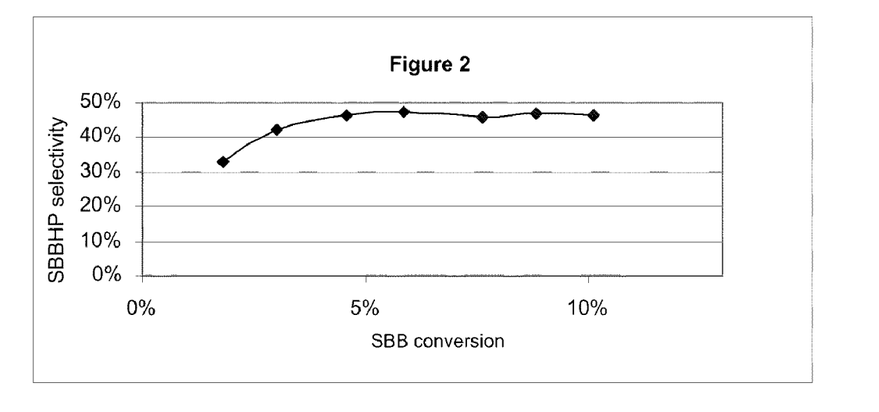
FIG. 2 is a graph of sec-butylbenzene conversion against sec-butylbenzene hydroperoxide selectivity for the barium-exchanged MnO molecular sieve catalyst of Example 2.

The process of Example 9 was repeated but with 0.2 g of the barium-exchanged catalyst of Example 2. A graph of the SBB conversion against the selectivity to sec-butylbenzene hydroperoxide (SBBHP) is shown in FIG. 2.

Example 11

SBB Oxidation Using Example 4 Catalyst

Figure 3:
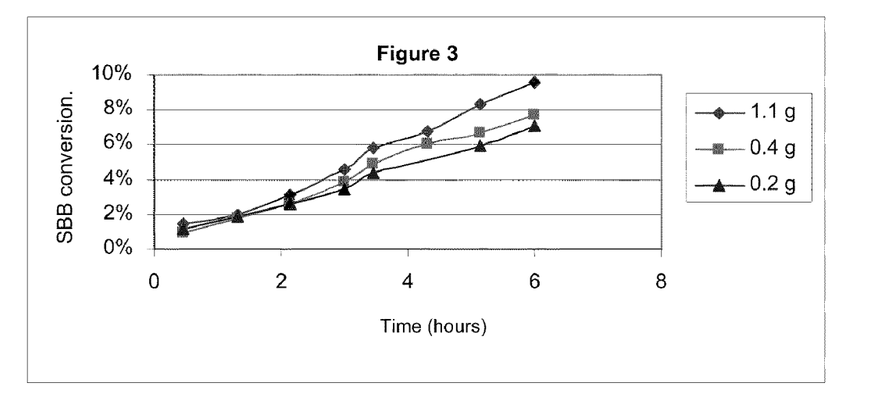
FIG. 3 is a graph of sec-butylbenzene conversion against time on stream using three different amounts of the barium-exchanged MnO molecular sieve catalyst of Example 4.
Figure 4:
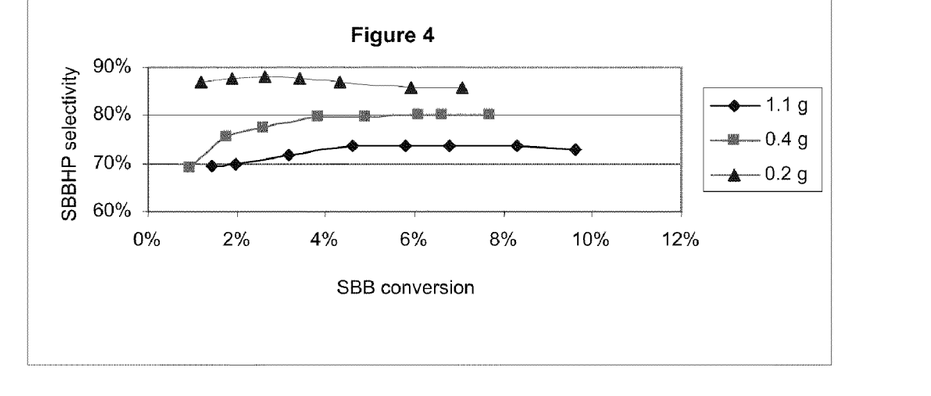
FIG. 4 is a graph of sec-butylbenzene conversion against sec-butylbenzene hydroperoxide selectivity for the barium-exchanged MnO molecular sieve catalyst of Example 4.

The process of Example 9 was repeated but with varying amounts (0.2 g, 0.4 g and 1.1 g) of the barium-exchanged catalyst of Example 4. A graph of the SBB conversion against time on stream is shown in FIG. 3 and a graph of the SBB conversion against the selectivity to sec-butylbenzene hydroperoxide (SBBHP) is shown in FIG. 4.

Example 12

SBB Oxidation Using Example 4 Catalyst

Figure 5:
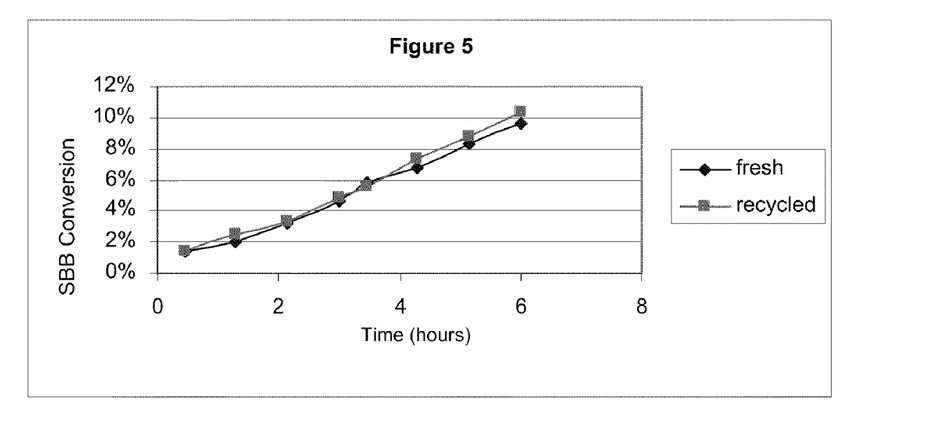
FIG. 5 is a graph comparing sec-butylbenzene conversion against time on stream for the fresh and recycled barium-exchanged MnO molecular sieve catalysts of Example 4.
Figure 6:
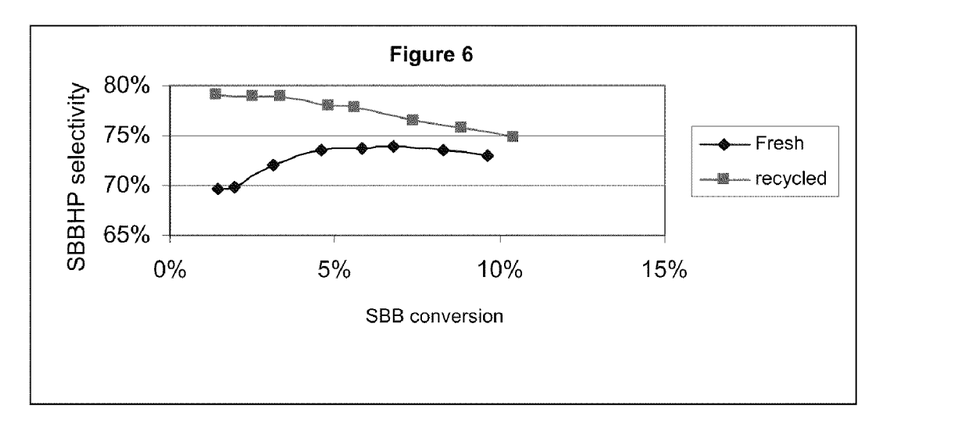
FIG. 6 is a graph comparing sec-butylbenzene conversion against sec-butylbenzene hydroperoxide selectivity for the fresh and recycled barium-exchanged MnO molecular sieve catalysts of Example 4.

To a 250-ml round bottom flask fitted with a condenser, stirrer and an air sparger, was charged 100 g of sec-butylbenzene (TCI) and 1.1 g of the barium-exchanged catalyst of Example 4. The flask was heated using a temperature-controlled heating mantle. Reaction temperature was 115° C. Reaction pressure was approximately atmospheric. The air flow rate was approximately 220 cc/min. Every 45 minutes, a small aliquot of the reaction mixture was removed from the flask and analyzed by GC. The test was run for 6 hours. At the end of the test the catalyst was filtered and recycled at the same conditions as mentioned above. A graph of the SBB conversion against time on stream is shown in FIG. 5 and a graph of the SBB conversion against the selectivity to sec-butylbenzene hydroperoxide (SBBHP) is shown in FIG. 6. The data shows no catalyst deactivation was observed after recycling and the catalyst selectivity was improved.

Example 13

SBB Oxidation Using Example 5 Catalyst

Figure 7:
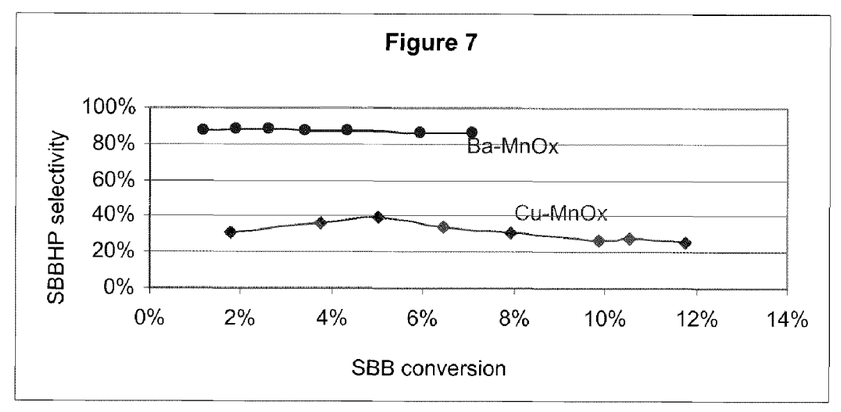
FIG. 7 is a graph comparing the sec-butylbenzene conversion against sec-butylbenzene hydroperoxide selectivity for the copper-exchanged MnO molecular sieve catalyst of Example 5 and for the barium-exchanged MnO molecular sieve catalyst of Example 4.

The process of Example 9 was repeated but with 0.2 g of the copper-exchanged catalyst of Example 5. A graph of the SBB conversion against the selectivity to sec-butylbenzene hydroperoxide (SBBHP) is shown in FIG. 7, which also plots the data for the barium-exchanged catalyst of Example 4. The data shows Cu ion exchange treatment results in higher catalyst activity but decreases the hydroperoxide selectivity.

Example 14

SBB Oxidation Using Example 6 Catalyst

Figure 8:
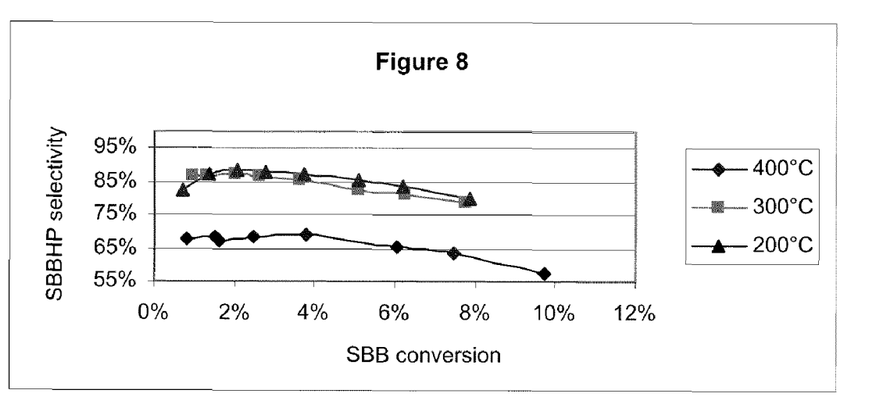
FIG. 8 is a graph of sec-butylbenzene conversion against sec-butylbenzene hydroperoxide selectivity for the unexchanged MnO molecular sieve catalysts of Example 6.

The process of Example 9 was repeated but with 0.2 g of each of the calcined catalysts of Example 6. A graph of the SBB conversion against the selectivity to sec-butylbenzene hydroperoxide (SBBHP) is shown in FIG. 8. The data shows that calcination at temperatures of 200° C. and 300° C. had no impact on activity or on selectivity. Calcination at 400° C. improved the catalyst activity but decreased the hydroperoxide selectivity.

Example 15

SBB Oxidation Using Example 7 Catalyst

Figure 9:
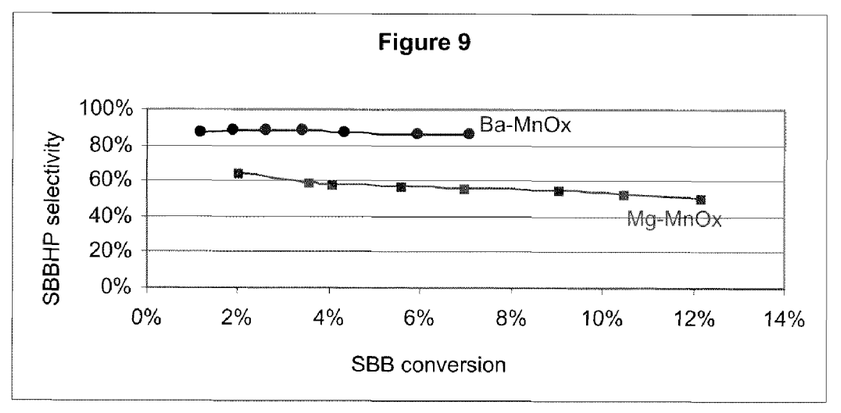
FIG. 9 is a graph comparing the sec-butylbenzene conversion against sec-butylbenzene hydroperoxide selectivity for the magnesium-exchanged MnO molecular sieve catalyst of Example 7 and for the barium-exchanged MnO molecular sieve catalyst of Example 4.

The process of Example 9 was repeated but with 0.2 g of the magnesium-exchanged catalyst of Example 7. A graph of the SBB conversion against the selectivity to sec-butylbenzene hydroperoxide (SBBHP) is shown in FIG. 9, which also plots the data for the barium-exchanged catalyst of Example 4. The data shows Mg ion exchange treatment results in higher catalyst activity but decreases the hydroperoxide selectivity.

Example 16

A solution was prepared by combining with stirring 600 grams of distilled water, 192 grams of an aqueous solution of 50% by weight sodium hydroxide, and 25.3 grams of potassium permanganate [$KMnO_4$]. Another solution was prepared by combining 600 grams of distilled water and 90 grams of manganese chloride tetrahydrate [$MnCl_2 \cdot 4H_2O$] with stirring. The second solution was slowly added to the first with stirring. The combined solution was allowed to age overnight. The mixture was then filtered and washed with distilled water and dried at 100° C. overnight. Three grams of the product was then added to 200 grams of distilled water and 26 grams of barium nitrate [$Ba(NO_3)_2$] with stirring for one hour. The pH of the mixture was then adjusted to 7 with the addition of 0.6 grams of ammonium hydroxide. The mixture was then filtered and air dried. A portion of the product was then air calcined in flowing air (50 cc/min) for 3 hours to produce a catalyst.

Example 17

A solution was prepared by combining with stirring 100 grams of distilled water, 320 grams of an aqueous solution of 50% by weight sodium hydroxide, and 20 grams of potassium permanganate [$KMnO_4$]. Another solution was prepared combining 300 grams of distilled water, 40.4 grams of manganese chloride tetrahydrate [$MnCl_2 \cdot 4H_2O$], and 12.4 grams of magnesium chloride [$MgCl_2$] with stirring. The second solution was slowly added to the first with stirring. The combined solution was allowed to age overnight. The mixture was then filtered and washed with distilled water and dried at 100° C. overnight. Three grams of the product was then added to 200 grams of distilled water and 26 grams of barium nitrate [$Ba(NO_3)_2$] with stirring for one hour. The pH of the mixture was then adjusted to 7 with the addition of ammonium hydroxide. The mixture was then filtered and air dried. A portion of the product was then air calcined in flowing air (50 cc/min) for 3 hours to produce a catalyst.

Example 18

A catalyst was prepared by combining 600 grams of DI water, 80 grams of potassium permanganate, and 10 grams of fumaric acid with stirring at room temperature. The mixture was then allowed to age at room temperature with no stirring then was filtered and washed. A portion of the dried sample was then calcined in air at 300° C. for three hours.

Example 19

Three grams of the product from Example 18 before the air calcination was then added to 200 grams of distilled water and 26 grams of barium nitrate [$Ba(NO_3)_2$] with stirring for one hour. The pH of the mixture was then adjusted to 7 with the addition of ammonium hydroxide. The mixture was then filtered and air dried. A portion of the product was then air calcined in flowing air (50 cc/min) for 3 hours.

Example 20

Three grams of the product from Example 18 before the air calcination was then added to 200 grams of distilled water and 26 grams of barium nitrate [$Ba(NO_3)_2$] with stirring for one hour. The pH of the mixture was then adjusted to 6 with the addition of ammonium hydroxide. The mixture was then filtered and air dried. A portion of the product was then air calcined in flowing air (50 cc/min) for 3 hours.

Example 21

Three grams of the product from Example 18 before the air calcination was then added to 200 grams of distilled water and 26 grams of barium nitrate [$Ba(NO_3)_2$] with stirring for one hour. The pH of the mixture was then adjusted to 8 with the addition of ammonium hydroxide. The mixture was then filtered and air dried. A portion of the product was then air calcined in flowing air (50 cc/min) for 3 hours.

Example 22

Three grams of the product from Example 18 before the air calcination was then added to 200 grams of distilled water and 26 grams of magnesium nitrate hexahydrate [$Mg(NO_3)_2 \cdot 6H_2O$] with stirring for one hour. The pH of the mixture was then adjusted to 7 with the addition of ammonium hydroxide. The mixture was then filtered and air dried. A portion of the product was then air calcined in flowing air (50 cc/min) for 3 hours.

Example 23

Three grams of the product from Example 18 before the air calcination was then added to 200 grams of distilled water and 26 grams of magnesium nitrate hexahydrate [$Mg(NO_3)_2 \cdot 6H_2O$] with stirring for one hour. The pH of the mixture was then adjusted to 6 with the addition of ammonium hydroxide. The mixture was then filtered and air dried. A portion of the product was then air calcined in flowing air (50 cc/min) for 3 hours.

Example 24

Three grams of the product from Example 18 before the air calcination was then added to 200 grams of distilled water and 26 grams of magnesium nitrate hexahydrate [$Mg(NO_3)_2 \cdot 6H_2O$] with stirring for one hour. The pH of the mixture was then adjusted to 8 with the addition of ammonium hydroxide. The mixture was then filtered and air dried. A portion of the product was then air calcined in flowing air (50 cc/min) for 3 hours.

Example 25

Three grams of the product from Example 17 before the air calcination was then added to 200 grams of distilled water and 26 grams of barium nitrate [$Ba(NO_3)_2$] with stirring for one hour. The pH of the mixture was then adjusted to 7 with the addition of ammonium hydroxide. The mixture was then filtered and air dried. A portion of the product was then air calcined in flowing air (50 cc/min) for 3 hours.

Example 26

Three grams of the product from Example 17 before the air calcination was then added to 200 grams of distilled water and 26 grams of barium nitrate [Ba(NO$_3$)$_2$] with stirring for one hour. The pH of the mixture was then adjusted to 6 with the addition of ammonium hydroxide. The mixture was then filtered and air dried. A portion of the product was then air calcined in flowing air (50 cc/min) for 3 hours.

Example 27

Three grams of the product from Example 17 before the air calcination was then added to 200 grams of distilled water and 26 grams of barium nitrate [Ba(NO$_3$)$_2$] with stirring for one hour. The pH of the mixture was then adjusted to 8 with the addition of ammonium hydroxide. The mixture was then filtered and air dried. A portion of the product was then air calcined in flowing air (50 cc/min) for 3 hours.

Example 28

Three grams of the product from a repeat of Example 18 before the air calcination was then added to 200 grams of distilled water and 26 grams of potassium nitrate [K(NO$_3$)] with stirring for one hour. The pH of the mixture was then adjusted to 7 with the addition of ammonium hydroxide. The mixture was then filtered and air dried. A portion of the product was then air calcined in flowing air (50 cc/min) for 3 hours.

Example 29

Three grams of the product from the repeat of Example 18 before the air calcination was then added to 200 grams of distilled water and 26 grams of potassium nitrate [K(NO$_3$)] with stirring for one hour. The pH of the mixture was then adjusted to 6 with the addition of ammonium hydroxide. The mixture was then filtered and air dried. A portion of the product was then air calcined in flowing air (50 cc/min) for 3 hours.

Example 30

Three grams of the product from the repeat of Example 18 before the air calcination was then added to 200 grams of distilled water and 26 grams of potassium nitrate [K(NO$_3$)] with stirring for one hour. The pH of the mixture was then adjusted to 8 with the addition of ammonium hydroxide. The mixture was then filtered and air dried. A portion of the product was then air calcined in flowing air (50 cc/min) for 3 hours.

Example 31

Three grams of the product from the repeat of Example 18 before the air calcination was then added to 200 grams of distilled water and 26 grams of cesium nitrate [Cs(NO$_3$)] with stirring for one hour. The pH of the mixture was then adjusted to 7 with the addition of ammonium hydroxide. The mixture was then filtered and air dried. A portion of the product was then air calcined in flowing air (50 cc/min) for 3 hours.

Example 32

Three grams of the product from the repeat of Example 18 before the air calcination was then added to 200 grams of distilled water and 26 grams of cesium nitrate [Cs(NO$_3$)] with stirring for one hour. The pH of the mixture was then adjusted to 6 with the addition of ammonium hydroxide. The mixture was then filtered and air dried. A portion of the product was then air calcined in flowing air (50 cc/min) for 3 hours.

Example 33

Three grams of the product from the repeat of Example 18 before the air calcination was then added to 200 grams of distilled water and 26 grams of cesium nitrate [Cs(NO$_3$)] with stirring for one hour. The pH of the mixture was then adjusted to 8 with the addition of ammonium hydroxide. The mixture was then filtered and air dried. A portion of the product was then air calcined in flowing air (50 cc/min) for 3 hours.

Example 34

SBB Oxidation with Different MnO Catalysts

To a 250-ml round bottom flask fitted with a condenser, stirrer and an air sparger, was charged 100 g of sec-butylbenzene (TCI) and 0.2 g of each of the catalysts of Examples 16 to 33. The flask was heated using a temperature-controlled heating mantle. Reaction temperature was 115° C. Reaction pressure was approximately atmospheric. The air flow rate was approximately 220 cc/min. A small aliquot of the reaction mixture was removed from the flask and analyzed by Gas Chromatography (GC). Each test was run for 6 hours and the results are summarized in Table 1 below.

TABLE 1

| Example | SBB Conv | SBBHP Sel. | 2-Phenyl-2-butanol Sel. | Acetophenone Sel. |
|---|---|---|---|---|
| 16 | 9.3% | 49.2% | 3.5% | 44.4% |
| 17 | 10.8% | 65.6% | 4.4% | 28.6% |
| 18 | 4.5% | 88.5% | 1.2% | 9.5% |
| 19 | 6.0% | 81.2% | 1.9% | 15.9% |
| 20 | 6.9% | 82.5% | 1.9% | 14.5% |
| 21 | 6.3% | 81.8% | 1.9% | 15.3% |
| 22 | 8.5% | 68.0% | 0.7% | 29.6% |
| 23 | 7.2% | 71.1% | 0.5% | 26.9% |
| 24 | 8.7% | 77.9% | 2.6% | 18.4% |
| 25 | 8.3% | 58.0% | 0.8% | 39.3% |
| 26 | 7.2% | 66.0% | 0.7% | 31.5% |
| 27 | 9.4% | 50.8% | 1.0% | 46.1% |
| 28 | 4.9% | 88.2% | 1.3% | 10.4% |
| 29 | 0.5% | 89.6% | 1.0% | 9.4% |
| 30 | 5.8% | 83.7% | 1.7% | 13.6% |
| 31 | 13.1% | 54.1% | 0.7% | 43.5% |
| 32 | 10.5% | 64.5% | 0.5% | 33.6% |
| 33 | 11.3% | 39.5% | 0.9% | 57.4% |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. A process for oxidizing an alkylaromatic compound to the corresponding hydroperoxide, the process comprising contacting an alkylaromatic compound of general formula (I):

(I)

in which R$^1$ and R$^2$ each independently represents an alkyl group having from 1 to 4 carbon atoms, provided that R$^1$ and R$^2$ may be joined to form a cyclic group having from 4 to 10 carbon atoms, said cyclic group being optionally substituted, and R$^3$ represents hydrogen, one or more alkyl groups having from 1 to 4 carbon atoms or a cyclohexyl group, with oxygen in the presence of a catalyst comprising a manganese oxide molecular sieve.

2. The process of claim 1, wherein the manganese oxide molecular sieve comprises $MnO_6$ octahedra which share edges to form a tunnel structure.

3. The process of claim 2, wherein the tunnel structure is of generally rectangular cross-section in which each side is defined by two or three $MnO_6$ octahedra.

4. The process of claim 1, wherein the manganese oxide molecular sieve is ion-exchanged with one or more metal cations.

5. The process of claim 4, wherein said one or more metal cations are selected from potassium, sodium, cesium, barium, magnesium, silver and copper.

6. The process of claim 1, wherein part of the manganese in the manganese oxide molecular sieve is replaced by one or more other divalent metal(s).

7. The process of claim 6, wherein said other divalent metals are selected from magnesium, cobalt, nickel, copper and zinc.

8. The process of claim 1, wherein the alkylaromatic compound of general formula (I) is selected from cumene, sec-butylbenzene, sec-pentylbenzene, p-methyl-sec-butylbenzene, 1,4-diphenylcyclohexane, sec-hexylbenzene, and cyclohexylbenzene.

9. The process of claim 8, wherein the alkylaromatic compound of general formula (I) is sec-butylbenzene or cyclohexylbenzene.

10. The process of claim 1, wherein said contacting is conducted at a temperature of 20° C. to 300° C.

11. The process of claim 10, wherein said contacting is conducted at a temperature of 50° C. to 130° C.

12. The process of claim 1, and further comprising converting the hydroperoxide into a phenol and an aldehyde or ketone of the general formula $R^1COCH_2R^2$ (III), in which $R^1$ and $R^2$ have the same meaning as in formula (I).

13. The process of claim 12, wherein converting the hydroperoxide is conducted in the presence of a catalyst.

14. The process of claim 13, wherein the catalyst is a homogeneous catalyst.

15. The process of claim 14, wherein the homogeneous catalyst comprises at least one of sulfuric acid, perchloric acid, phosphoric acid, hydrochloric acid, p-toluenesulfonic acid, ferric chloride, boron trifluoride, sulfur dioxide and sulfur trioxide.

16. The process of claim 13, wherein the catalyst is a heterogeneous catalyst.

17. The process of claim 16, wherein the heterogeneous catalyst comprises a smectite clay.

18. The process of claim 12, wherein converting the hydroperoxide is conducted at a temperature of 40° C. to 120° C. and/or a pressure of 100 to 1000 kPa and/or a liquid hourly space velocity (LHSV) based on the hydroperoxide of 1 to 50 $hr^{-1}$.

19. The process of claim 12, wherein the hydroperoxide is cyclohexylbenzene hydroperoxide and its conversion product comprises phenol and cyclohexanone, which process further comprises dehydrogenating the cyclohexanone to produce further phenol.

20. A process for producing a phenol, said process comprising:
(a) contacting an alkylaromatic compound of general formula (I):

in which $R^1$ and $R^2$ each independently represents an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, with oxygen in the presence of a catalyst comprising a manganese oxide molecular sieve to produce a hydroperoxide of general formula (II):

in which $R^1$, $R^2$ and $R^3$ have the same meaning as in formula (I), and
(b) converting the hydroperoxide of formula (II) into a phenol and an aldehyde or ketone of the general formula $R^1COCH_2R^2$ (III), in which $R^1$ and $R^2$ have the same meaning as in formula (I).

21. The process of claim 20, wherein said manganese oxide molecular sieve comprises $MnO_6$ octahedra which share edges to form a tunnel structure.

22. The process of claim 20, wherein the tunnel structure is of generally rectangular cross-section in which each side is defined by two $MnO_6$ octahedra.

23. The process of claim 20, wherein the tunnel structure is of generally rectangular cross-section in which each side is defined by three $MnO_6$ octahedra.

* * * * *